(12) United States Patent
Hendriks et al.

(10) Patent No.: US 7,262,283 B2
(45) Date of Patent: Aug. 28, 2007

(54) METHOD FOR EXTRACTING PROTEINS

(75) Inventors: Robertus Hendriks, Heidelberg (DE); Afsaneh Abdolzade-Bavil, Eppelheim (DE)

(73) Assignee: Merck Patent GmbH, Darmstadt (DE)

( * ) Notice: Subject to any disclaimer, the term of this patent is extended or adjusted under 35 U.S.C. 154(b) by 189 days.

(21) Appl. No.: 10/525,991

(22) PCT Filed: Aug. 8, 2003

(86) PCT No.: PCT/EP03/08806

§ 371 (c)(1), (2), (4) Date: Mar. 1, 2005

(87) PCT Pub. No.: WO2004/020646

PCT Pub. Date: Mar. 11, 2004

(65) Prior Publication Data

US 2006/0166267 A1    Jul. 27, 2006

(30) Foreign Application Priority Data

Sep. 2, 2002    (EP) .................................. 02019570

(51) Int. Cl.
*C07K 1/14*    (2006.01)
(52) U.S. Cl. ..................................... 530/412
(58) Field of Classification Search .................... None
See application file for complete search history.

(56) References Cited

U.S. PATENT DOCUMENTS 6,090,784 A * 7/2000 Warren ......................... 514/16

FOREIGN PATENT DOCUMENTS

JP    61-176518    *    8/1986

OTHER PUBLICATIONS

Ramsby et al. (1994): Differential detergent fractionation of isolated hepatocytes Electrophoresis 15(2) 265-77.

Sinibaldi R M et al: "Putative function of drosophila-Melanogaster heat shock proteins in the nucleoskeleton" Journal of Biological Chemistry, Bd. 256, Nr. 21, 1981, 10735-107-38, XP002266600.

Fey E G et al: "Epithelial Cytoskeletal framework and nuclear matirx intermediate filament scaffold 3 dimensional organization and protein composition" journal of cell biology, Bd. 98, Nr. 6, 1984 XP002266743.

Ramsby et al (1999): Differential detergent fractionation of eukaryotic cells in Methods in Molecular Biology, vol. 112: 2-D proteome Analysis Protocols Andrew J. Link (Editor, Humana Press Totowa New Jersey, 1999.

Patton W.F. (1999): Protein subcellular redistribution: linking physiology to genomics via the proteome and separation technologies J. Chrom B, 722, 203-223.

Chiang et al.(2000): NFkappaB translocation in human microvessel endothelial cells using a four-compartment subcellular protein redistribution assay J.Biochem.Biophys Meth. 46-53-68.

Jimi et al. (1998): Activation of NFkappaB is involved in the survival of osteoclasts promoted by interleuin-1 J.Biol.Chem 273-8799-805.

Mejdoubi et al. (1999): NFkappaB is involved in the induction of the rat hepatic alpha-1acid glycoprotein gene by Phenobarbital Biochem Biophys Res.Commun. 254, 93-9.

Butcher et al (2001): Toxoplasma gondii tachyzoites inhibit proinflammatory cytokine induction in infected macrophages by preventing nuclear translocation of the transcription factor NFkappaB J.Immun. 167(4), 2193-201.

Nature Insight Proteomics; Barbara Marte; Senior Editor pp. 191-239.

* cited by examiner

*Primary Examiner*—Robert A. Wax
(74) *Attorney, Agent, or Firm*—Miller, White, Zelano, Branigan, P.C.

(57) ABSTRACT

The present invention relates to a method and a kit for the sequential extraction of proteins for the production of partial proteomes from a complete proteome. In particular, the method according to the invention, besides other partial proteomes, gives a partial proteome of proteins from the cell nucleus interior separated from proteins of the cytoskeleton and of the nuclear matrix.

23 Claims, 11 Drawing Sheets

A

B

METHOD FOR EXTRACTING PROTEINS

The invention relates to a method for the extraction of cellular proteins depending on their subcellular localisation (topology). In particular, the method according to the invention facilitates the isolation of proteins from the cell nucleus interior as an independent fraction by separating the complete proteome into partial proteomes and thus makes this fraction available for further analyses for the first time in adequate purity and quality.

With the sequencing of the human genome, science has gained access to the individual genetic code of each human being. This provides information on his/her descent and origin. However, this information is inadequate for investigation of the biological function of individual genes or the corresponding proteins. The complex network of a cell cannot be characterised simply by decoding the genomic DNA of a human being. The genomic analysis must be followed by an investigation of the proteins encoded by the genome, since it is only with this additional information that the dynamic functioning of the human organism can be described at a molecular level. In addition, there is frequently only a minor correlation between gene transcription and the corresponding translation product, and consequently it is only with the aid of proteome analysis that it can be determined which proteins are expressed to what extent and possibly modified post-translationally under given influences (Allen, L.: Functional Genomics *Nature* 405 (2000) 819–865; Ezzell, C.: The Business of the Human Genome *Scientific American* July (2000) 39–57).

In order to be able to investigate proteins, for example, with respect to their expression pattern or their function, they first have to be made available for the corresponding analyses.

Parallel separation and analysis of all proteins in a cell is virtually impossible using today's methods. A human cell expresses between 35,000 and 50,000 proteins, which vary in abundance by a factor of $10^6$. Even the protein separation technique that currently has the highest resolution, two-dimensional gel electrophoresis, can separate a maximum of 5,000 to 10,000 proteins with high resolution, with it being possible principally to visualise the proteins having a high expression rate from a complete lysate. However, since in most cases low-abundance proteins tend to be more involved in pathological processes, fractionation of the proteins in a cell into sub-units, i.e. the production of partial proteomes, is necessary from clinical and diagnostic points of view before the protein analysis.

In order to clarify the function of a protein, various basic techniques, such as, for example, activity assays or protein interaction analyses, have been developed. However, these usually require that the proteins to be analysed are provided in native, non-denatured state for the respective functional analysis.

A valuable supplementary approach for investigating the function of proteins is analysis of the subcellular localisation of proteins or the redistribution thereof in a cell. Many regulation processes in a cell result in modification of the subcellular localisation after interaction with a signal molecule, with a change in RNA transcription being caused, for example by transfer of a protein from the cytosol into the cell nucleus.

There is thus increasing demand for standardised methods for the production of partial proteomes which on the one hand cause a reduction in the total number of proteins to be analysed in parallel and on the other hand allow the subcellular localisation (topology) to be included as additional information in the functional proteome analysis.

Various methods are known for the production of partial proteomes, but, due to the type of purification, they each only make part of the proteome available for analysis. Examples of such methods are the purification of separated cell compartments based either on different net charge or different density of the compartments, on different protein composition, which can be utilised for affinity purification, or on different solubility of the organelle proteins in the presence of specific buffers.

Since only part of the complete proteome of a cell is made available for analysis in these methods, proteins which are not present in the particular purified partial proteome are not available for further analysis. In addition, the investigation of a topological redistribution of proteins is not possible. Prior separation of the sample collective and parallel production of different partial proteomes can only overcome the above-mentioned disadvantages to a limited extent, since this variant is firstly very labour-intensive and secondly entails the risk that the samples are not homogeneous. In addition, the amount of sample available is frequently so small that splitting of the sample is impossible.

It would therefore be desirable to have a method which enables the entire sample to be separated into various partial proteomes in a sequential method, with all proteins of the sample ultimately being available for further analyses as a constituent of one of the partial proteomes.

A known method for the sequential purification of a plurality of cell compartments is selective detergent extraction [1, 2], in which four fractions (partial proteomes) are obtained. In the first step, a cytosolic fraction is obtained, in which the soluble proteins of the cytosol and soluble components of the cytoskeleton are enriched. In the second step, a fraction containing proteins of the membrane/organelles is obtained. The third step gives a 'nuclear' fraction, in which, according to the authors, proteins of the nuclear membrane and soluble nuclear proteins are enriched. In the fourth and final step, a fraction containing proteins of the detergent-resistant cytoskeleton and of the nuclear matrix is formed.

Since the date of publication of the original method in 1994, various modifications have been introduced, all of which have concentrated exclusively on the final extraction step after solubilisation of the cell nucleus (summarised in Patton, 1999 [3]). The method described was employed for the investigation of the subcellular redistribution of a transcription factor [4] which is involved in signal transduction by cytokines and, after cytokine-induced translocation into the nucleus, is able to bind directly to the DNA [5, 6, 7]. According to the authors' results, however, soluble and/or DNA-associated cell nuclear proteins, in particular, together with proteins of the cytoskeleton and nuclear matrix were only obtained in the final and denaturing extraction step.

This means that the methods known to date for the sequential purification of a plurality of cell compartments by selective detergent extraction [1, 2, 3] do not enable unambiguous topological assignment of nuclear proteins since an independent fraction separated from components of the cytoskeleton and containing, in particular, the proteins from the cell nucleus interior is not obtained.

A further disadvantage of the known extraction method is that the transcription factors are also present in the fourth fraction. Since transcription factors typically occur in a significantly smaller amount than cytoskeleton proteins, their detection and analysis is made significantly more difficult by the presence of the cytoskeleton proteins.

In addition, subsequent functional analysis of the proteins present in the fourth fraction is greatly restricted since sodium dodecylsulfate (SDS) is employed in the isolation of this fraction. This denatures the proteins, meaning that they are no longer available for important analytical methods, such as, for example, co-immunoprecipitation, enzyme activity tests or electrophoretic mobility shift assay (EMSA). This is likewise a crucial barrier to subsequent functional analysis of this important regulatory protein class.

These problems were not recognised in any of the applications carried out since 1994 or modifications to the extraction protocol, let alone improvements proposed in this respect.

In eukaryotic cells, however, it is precisely the proteins of the cell nucleus that are of major importance for a very wide variety of functions of the cell. The cell nucleus makes up about 10% of the total volume of a eukaryotic cell and is surrounded by a nuclear sheath consisting of two membranes. The nuclear sheath is connected directly to the endoplasmatic reticulum and is connected to two networks of intermediary filaments: firstly a thin layer of filaments (nuclear lamina) in the cell nucleus interior, which supports the inner cell membrane, and secondly less regularly organised intermediary filaments which surround the outer nuclear membrane. These intermediary filament networks thus give the nuclear sheath a certain stability. The nuclear sheath surrounds the nucleoplasm, which contains, inter alia, chromatin (DNA and proteins associated therewith) and the nucleolus. The nuclear proteins in the nucleoplasm, i.e. in the cell nucleus interior, include, in particular, DNA-binding proteins, such as histones and non-histone proteins (for example HMGs and transcription factors), RNA-binding proteins, which are involved in RNA splicing and transport, and skeleton-associated proteins. The proteins which form the skeleton in the cell nucleus interior, in particular the lamina, are, in this description, not regarded as part of the nucleoplasm or of the cell nucleus interior. In particular, DNA-binding proteins, such as histones and non-histone proteins (for example HMGs and transcription factors), RNA-binding proteins, which are involved in RNA splicing and transport, and skeleton-associated proteins are therefore regarded below as proteins from the cell nucleus interior.

Various methods are described in the literature for the separate solubilisation of cell nucleus proteins, inter alia using high salt concentrations ($\geq 1$ M), it being known that high salt concentrations in the extraction buffer interfere with protein interactions and thus with the further functional analyses, such as, for example, analysis of protein complexes. In addition, high salt concentrations in the extracted fractions impair all subsequent protein analysis methods, such as, for example, isoelectric focusing (IEF), enzyme activity tests, EMSA, ELISA, SDS-PAGE and 2DE. Furthermore, high salt concentrations readily attack cytoskeleton and cytoskeleton-associated proteins, which can cause contamination of the cell nucleus protein fraction by cytoskeleton proteins.

The object of the present invention was therefore to provide a method which, in the course of sequential separation of the complete proteome into partial proteomes, also facilitates the production, in addition to further partial proteomes, of a partial proteome of the proteins from the cell nucleus interior without significantly denaturing the proteins from the cell nucleus interior in the process.

It has been found that, during the production of partial proteomes from the complete proteome of a cell preparation, from the cell nucleus preparation obtained, inter alia, after removal of the cytosolic proteins and the proteins of the membrane/organelles, the liberation of proteins from the cell nucleus interior is effected efficiently and surprisingly simply without significantly impairing the integrity of the cytoskeleton if the cell nucleus preparation is extracted with a salt and detergent solution according to the invention and preferably additionally with a nuclease.

Since the proteins of the detergent-resistant cytoskeleton and the nuclear matrix are not co-extracted to a significant extent during preparation of the partial proteome of the proteins from the cell nucleus interior, these can be obtained as an independent fraction in a subsequent sequential method step.

The present invention therefore relates to a method for the sequential production of partial proteomes from the complete proteome of a cell preparation, characterised by the following method steps:

a) provision of a sample containing a cell preparation
b) extraction of the cytosolic proteins and the membrane/organelle proteins from the sample provided in step a), leaving a cell nucleus preparation
c) extraction of the proteins from the cell nucleus interior from the cell nucleus preparation obtained in step b) by treatment with an extraction buffer having a pH of between 6.5 and 8 which comprises at least the following constituents:

in total from 0.1 to 7 percent by weight of one or more nonionic detergents in total from 0.05 to 3 percent by weight of one or more cholic acid derivatives one or more salts from the group consisting of the alkali metal and/or ammonium salts in a total concentration of between 75 and 500 mmol/l, where detergent-resistant proteins of the cytoskeleton and of the nuclear matrix are not extracted to a significant extent together with the proteins from the cell nucleus interior, but instead remain in the extraction residue. The extract obtained in step c) is accordingly a partial proteome enriched with proteins from the cell nucleus interior.

In a preferred embodiment, the extraction buffer employed in step c) additionally comprises a nuclease.

In a preferred embodiment, the extraction buffer employed in step c) comprises polyoxyethylene sorbitan monopalmitate (Tween® 40) as nonionic detergent, deoxycholate as cholic acid derivative and NaCl as alkali metal salt.

In a preferred embodiment, the extraction of the cytosolic proteins and the membrane/organelle proteins in step b) is carried out by:

b i) extraction of the cytosolic proteins from the sample provided in step a) by selective permeabilisation of the plasma membrane without significantly impairing the integrity of the subcellular membrane/organelle structures, the cell nucleus and the cytoskeleton. The extract obtained is a partial proteome enriched with cytosolic proteins.

b ii) extraction of the membrane/organelle proteins from the part of the sample remaining after the extraction in step b i) with retention of the structural integrity of cell nucleus and cytoskeleton. The extract obtained is a partial proteome enriched with membrane/organelle proteins.

In a preferred embodiment, the proteins of the detergent-resistant cytoskeleton and of the nuclear matrix are, in an additional method step d), extracted as a further partial proteome from the extraction residue remaining in step c).

The present invention also relates to the use of the method according to the invention in the investigation of the redistribution of proteins or the functional analysis of proteins.

The present invention additionally relates to a protein extraction kit at least containing an extraction buffer having a pH of between 6.5 and 8 which comprises at least the following constituents:

in total from 0.1 to 7 percent by weight of one or more nonionic detergents in total from 0.05 to 3 percent by weight of one or more cholic acid derivatives one or more salts from the group consisting of the ammonium and/or alkali metal salts in a total concentration of between 75 and 500 mmol/l.

In a preferred embodiment, the kit additionally contains a nuclease which can be added to the extraction buffer.

In a preferred embodiment, the kit additionally contains buffer for extraction of the cytosolic proteins and/or the membrane/organelle proteins from cell preparations and a buffer for extraction of the proteins of the detergent-resistant cytoskeleton and of the nuclear matrix. The method according to the invention can be carried out with this preferred embodiment of the kit for the production of four partial proteomes from the complete proteome of a cell preparation.

The explanations for FIGS. 1 to 11 are given in Examples 1 to 12.

The method according to the invention facilitates for the first time the separation of the complete proteome of a cell preparation into a plurality of subcellular partial proteomes, with one of the partial proteomes being enriched with proteins from the cell nucleus interior. A topological assignment and functional analysis is thus facilitated for the first time by an extraction method.

For the purposes of the invention, the term partial proteome of the proteins from the cell nucleus interior means a partial proteome in which principally proteins from the cell nucleus interior are enriched. The partial proteome of the proteins from the cell nucleus interior according to the invention comprises no or only a small proportion, which does not interfere with the further functional analyses, of detergent-resistant proteins of the cytoskeleton and of the nuclear matrix. Furthermore, the proteins in the partial proteome of the proteins from the cell nucleus interior obtainable by the method according to the invention are in substantially non-denatured form. This means that denaturing of the proteins by the extraction buffer employed in step c) in accordance with the invention is avoided so substantially that an adequate proportion of the partial proteome obtained in step c) can be provided for further functional analysis.

The cell preparation employed in the method according to the invention can be eukaryotic cells, for example cells cultivated in suspension or adherent cells. Cell preparations from tissue can also be employed, giving cells or cell groups, by dividing tissue by means of biochemical, enzymatic and/or physical means. The cell preparation may also comprise other eukaryotic cells, such as, for example, spheroplasts from yeast cells, plant cells after removal of the cell wall or insect cells, and cell preparations from fungi. The cell preparation employed in the method according to the invention preferably comprises eukaryotic tissue culture cells from mammals.

The term cell nucleus preparation is applied in accordance with the invention to residues of the cell preparation from which the cytosolic proteins and the membrane/organelle proteins have been removed in advance. During removal of these proteins, it must be ensured that the cell nuclei present in the resultant cell nucleus preparation are still intact to the extent that the proteins from the cell nucleus interior are still predominantly in the cell nucleus preparation and have not already been removed during the removal of the cytosolic proteins and the membrane/organelle proteins. This condition is ensured, for example, by the buffer systems recommended below for the extraction of the cytosolic proteins and the membrane/organelle proteins. Furthermore, a cell nucleus preparation prepared by removal of the cytosolic proteins and the membrane/organelle proteins from cell preparations usually also comprises constituents of the cytoskeleton.

The method according to the invention facilitates the division of the complete proteome of the cell preparation into at least three partial proteomes, one of which is enriched with the proteins from the cell nucleus interior. Besides the partial proteome of the proteins from the cell nucleus interior, various other partial proteomes may be produced. The nature of the further partial proteomes is dependent on the type of extraction carried out in step b) and the extraction steps carried out after the extraction of the partial proteome of the proteins from the cell nucleus interior (step c).

For example, the cytosolic proteins and membrane/organelle proteins extracted in step b) can be extracted in parallel in the form of a partial proteome or preferably sequentially, giving two partial proteomes (one partial proteome enriched with cytosolic proteins, one partial proteome enriched with membrane/organelle proteins). For the purposes of the invention, "enriched" means that the proteins referred to as "enriched" are predominantly present in the particular partial proteome. Other proteins are only present in an amount which does not significantly impair further analysis of the enriched proteins.

In a preferred embodiment, the selective permeabilisation of the plasma membrane of the cells in step b) for extraction of the cytosolic proteins is effected without significant impairment of other cellular sub-structures by chemical treatment with a saponin which is preferentially incorporated into cholesterol-rich membranes, in particular with a digitonin-containing buffer. Alternatively, this could also be effected by means of other substances, such as, for example, streptolysin-O, enzymatic treatment with, for example, lipase or the action of mechanical forces by means of, for example, electroporation, freezing/thawing, filter ripping, or combinations thereof. Such methods are described in the literature and are known to the person skilled in the art. The extract obtained is a partial proteome enriched with cytosolic proteins.

After extraction of the cytosolic proteins, the membrane/organelle proteins are extracted from the extraction residue with substantial retention of the structural integrity of cell nucleus and cytoskeleton. Suitable for this purpose are, for example, nonionic detergents or zwitterionic detergents under mild conditions. In particular, Triton® X-100 is suitable for this purpose. These methods are also described in the literature and are known to the person skilled in the art. The extract obtained is a partial proteome enriched with membrane/organelle proteins. The extraction residue obtained is a cell nucleus preparation, which can be passed on to method step c).

If the properties of the cell nucleus preparation with respect to retention of the structural integrity of the cell nucleus or cell nuclei for step c) are not significantly changed, the extraction of the cytosolic and membrane/organelle proteins in step b) can also be carried out with other agents. It is furthermore possible also to carry out step b) in more than two extraction steps in order to produce more than two partial proteomes. However, separation in two sub-steps to produce a partial proteome which is enriched with cytosolic proteins and a partial proteome which is enriched with membrane/organelle proteins is preferred.

In order to produce only one partial proteome which comprises both the cytosolic and the membrane/organelle proteins in step b), it is sufficient to treat the cell preparation from step a) with reagents as described above for the extraction of the membrane/organelle proteins, i.e. with nonionic detergents or zwitterionic detergents under mild conditions. Preference is given here to detergents having an HLB value of between 12 and 20 for the non-denaturing solubilisation of membrane proteins. In particular, detergents having a high aggregate number, such as, for example, Triton® X-100 and NP-40, are suitable for this purpose. Prior treatment for selective extraction of cytosolic proteins (such as treatment with a digitonin-containing buffer or with streptolysin-O, enzymatic treatment with, for example, lipase or the action of mechanical forces by means of, for example, electroporation, freezing/thawing, filter ripping, or combinations thereof) is generally not necessary.

The cell nucleus preparation obtained after extraction of the cytosolic proteins and the membrane/organelle proteins is then, in accordance with the invention, subjected to selective detergent extraction of the proteins from the cell nucleus interior in step c).

For the method according to the invention, it is of great importance in step c), the production of a partial proteome which is enriched with proteins from the cell nucleus interior, that the majority of the proteins from the cell nucleus interior are bound to bonding partners, such as nucleic acids or other proteins. The strength of the bond formed by the proteins from the cell nucleus interior to their respective bonding partners varies greatly and is partially dependent on the environment present. Thus, for example, the interaction of histones with DNA molecules is significantly stronger than that of HMGs. In the method according to the invention, the bonding of the proteins from the cell nucleus interior to their bonding partners, in particular nucleic acids, can be employed in a targeted manner for further selection of the proteins from the cell nucleus interior. Depending on the choice of extraction buffer, weakly bonded, strongly bonded proteins from the cell nucleus interior or all proteins from the cell nucleus interior can be extracted to an increased extent, virtually independently of their bonding strength to the respective bonding partners, in particular nucleic acids.

The extraction buffer used in step c) typically has a pH of between 6.5 and 8. At lower pH values, problems can arise, in particular, with the solubility of certain constituents, such as the nonionic detergents or the cholic acid derivatives. The preferred pH range is between pH 6.9 and pH 7.8. Suitable buffer substances are therefore those which buffer in the weakly acidic to weakly alkaline range, such as MOPSO, BES, MOPS, phosphate or preferably PIPES. The buffer concentration is typically 2–100 mM, preferably between 5 and 20 mM.

Furthermore, the extraction buffer used in accordance with the invention comprises one or more suitable nonionic detergents in a proportion of typically in total from 0.1 to 7% by weight, in any case above the CMC, preferably between 0.2 and 5% by weight. An increase in the detergent concentration beyond the stated range entails the risk that increased denaturing of proteins occurs. In addition, high detergent concentrations can interfere with the later analytical methods.

Important features for the differentiation of detergents are, for example, the HLB value, CMC and the aggregate number.

Nonionic detergents which are suitable in accordance with the invention are those which, in the concentration selected in accordance with the invention in combination with the other constituents of the extraction buffer, have the effect that the cell nucleus structure previously present is dissolved. It is important here that the cell nucleus morphology previously present is destroyed and the nucleoplasm proteins are liberated without a significant proportion of the cytoskeleton proteins being liberated. Nonionic detergents which are particularly suitable in accordance with the invention are, for example, those containing a hydrophilic polyoxyethylene head group containing no phenyl ring between alkyl chain and head group, preferably Tween® detergents, in particular polyoxyethylene sorbitan monopalmitate (Tween® 40).

A further essential constituent of the extraction buffer used in accordance with the invention is one or more cholic acid derivatives. Cholic acid derivatives which are suitable in accordance with the invention are anionic detergents. They have a steroid backbone carrying one or more identical or different side chains, such as, for example, —OH, —CH$_3$, C$_2$H$_5$ or, for example, amino acids, and a carboxyl group at the end of an alkyl chain. Particularly suitable are cholic acid derivatives which—in contrast to nonionic detergents, such as Triton—have a low aggregate number. For the purposes of the invention, cholic acid derivatives are also taken to mean cholic acid itself and salts of cholic acid. The cholic acid derivative employed is preferably Na deoxycholate.

In the extraction buffer employed in accordance with the invention in step c), one or more cholic acid derivatives are used in a proportion of typically in total from 0.05 to 3 percent by weight, preferably from 0.1 to 2.5% by weight. Here too, an increase in the proportion beyond the stated range can cause denaturing of the proteins and/or interference with the further analyses.

The extraction buffer furthermore comprises one or more alkali metal and/or ammonium salts in a concentration of between 75 and 500 mmol/l. An increase in the salt concentration beyond the stated concentration range can cause denaturing of the proteins and/or interference with the further analyses.

Preference is given in accordance with the invention to alkali metal salts, in particular sodium salts, such as nitrates, sulfates, phosphates and particularly halides, such as bromides or chlorides. NaCl is particularly preferred.

An extraction buffer for step c) which is particularly preferred in accordance with the invention comprises about 10 mM PIPES, about 1% by weight of Tween® 40, about 0.5% by weight of Na deoxycholate and about 350 mM NaCl. In addition, the extraction buffer for step c) may comprise further constituents, such as, for example, stabilisers or preservatives.

In a preferred embodiment of the method, the extraction buffer for step c) additionally comprises a nuclease, preferably an endonuclease from *Serratia marcescens* (Benzonase® from Merck KGaA, Darmstadt). For the activity of the nucleases, it is usually advantageous additionally to add alkaline earth metal salts to the extraction buffer, typically in a concentration of between 0.02 and 10 mmol/l. Particularly suitable salts and the concentration thereof should be selected depending on the nuclease used. On use of Benzonase®, MgCl$_2$, for example, in a concentration of between 1 and 10 mM, in particular between 1 and 2 mM, is suitable.

The suitable amount and activity of the nuclease employed depends on the target duration of the extraction step. The more nuclease is added, the faster the extraction can be carried out. However, it must be borne in mind here that the partial proteome obtained in the extraction is also contaminated with the nuclease. The more nuclease is employed, the more nuclease is also present in the partial proteome which is enriched with the proteins from the cell nucleus interior. It must be noted that nucleases interfere with certain protein analysis methods, such as, for example, EMSA. If the partial proteome which is enriched with the proteins from the cell nucleus interior is to be subjected to an analytical method of this type, the addition of nucleases must be avoided.

As can be seen from Examples 4 and 5, the addition of nuclease can influence whether weakly bound or strongly bound proteins from the cell nucleus interior are preferentially extracted. If no nuclease is added to the buffer, the proportion of strongly nucleic acid-bound proteins, such as the histones, is reduced.

The integrity of the cytoskeleton is not significantly impaired by method step c) according to the invention for the production of a partial proteome of the proteins from the cell nucleus interior, meaning that the method according to the invention can give for the first time a fraction enriched in the low-abundance nuclear proteins and separated from the high-abundance components of the cytoskeleton.

In addition, following step c), the proteins of the detergent-resistant cytoskeleton and of the nuclear matrix can be extracted from the remaining extraction residue as a further partial proteome by known methods in a subsequent extraction step. Suitable for this purpose are, for example, SDS-containing denaturing buffers. These buffers may additionally comprise reducing agents, such as, for example, DTT or β-mercaptoethanol.

The method according to the invention is simple, efficient and automatable and significantly simplifies the detection and analysis of the low-abundance and simultaneously pharmacologically most interesting regulatory protein classes (membrane proteins, such as, for example, receptors on the plasma membrane or DNA-associated proteins and transcription factors). This is achieved by simple and selective removal of high-abundance proteins (for example household proteins in the cytosol and also cytoskeleton proteins). The method allows for the first time the examination of functional proteins of the cell nucleus separately from the cytoskeleton without the loss of other partial proteomes. The partial proteomes obtained can be subjected to a multiplicity of established protein analysis techniques. This also allows, for example, functional studies by means of enzyme activity assays or electrophoretic mobility shift assay (EMSA) for cell nuclear proteins. In addition, the method according to the invention facilitates not only the topological assignment of cellular proteins, but also the analysis of the dynamic redistribution of the said protein classes into the various cellular compartments, including the cell nucleus, which was not possible by previous approaches. An analysis of this type provides important information on the function of the protein investigated. Linked to common techniques, such as, for example, mass spectrometry (MS), 2D gel electrophoresis (2DE), amino acid sequencing or immunoblotting, comprehensive analysis of the proteins present in the cell and the subcellular distribution thereof can be employed in order to identify novel proteins or protein functions and to indicate their involvement in certain cellular signal pathways. The method according to the invention thus represents a fundamental approach for characterising both physiological and also pathophysiological cellular processes or changes which arise, inter alia, due to diseases or under the influence of medicaments/substances.

The present invention additionally relates to a protein extraction kit, in particular for the production of partial proteomes from a complete proteome present in a cell preparation, at least containing an extraction buffer having a pH of between 6.5 and 8, which at least comprises the following constituents:

in total from 0.1 to 7 percent by weight of one or more nonionic detergents in total from 0.05 to 3 percent by weight of one or more cholic acid derivatives one or more salts from the group consisting of the ammonium and/or alkali metal salts in a total concentration of between 75 and 500 mmol/l.

The preferred amounts of the individual constituents indicated for the extraction buffer for step c) likewise apply to the extraction buffer in the kit. The buffer is typically in the form of a dry reagent mixture for dissolution in water, in the form of an aqueous concentrate or for direct use in aqueous form.

In a preferred embodiment, the kit furthermore contains a nuclease for addition to the extraction buffer.

In a preferred embodiment, the kit additionally contains buffers for extraction of the cytosolic proteins and/or the membrane/organelle proteins from cell preparations. The kit particularly preferably contains reagents for carrying out the preferred embodiment of the method according to the invention in which four partial proteomes (partial proteome enriched with cytosolic proteins, partial proteome enriched with membrane/organelle proteins, partial proteome enriched with proteins from the cell nucleus interior, partial proteome enriched with proteins of the cytoskeleton and of the nuclear matrix) are obtained from the complete proteome of a cell preparation.

The kit may equally have further constituents or reagents, such as equipment and consumables suitable for carrying out the method according to the invention and/or reagents for further processing of the partial proteomes, for example for functional analysis or storage.

Even without further comments, it is assumed that a person skilled in the art will be able to utilise the above description in its full scope. The preferred embodiments and examples should therefore merely be regarded as descriptive disclosure which is absolutely not limiting in any way.

The complete disclosure content of all applications, patents and publications mentioned above and below, and of the corresponding application EP 02019570.7, filed on 02 Sep. 2002, is incorporated into this application by way of reference.

BIBLIOGRAPHY

[1] Ramsby et al. (1994): "Differential detergent fractionation of isolated hepatocytes" *Electrophoresis* 15(2) 265–77

[2] Ramsby et al. (1999): "Differential detergent fractionation of eukaryotic cells" in Methods in Molecular Biology, Volume 112: "2-D proteome Analysis Protocols" Andrew J. Link (Editor, Humana Press Totowa N.J., 1999

[3] Patton W. F. (1999): "Protein subcellular redistribution: linking physiology to genomics via the proteome and separation technologies" *J. Chrom B*, 722, 203–223

[4] Chiang et al. (2000): "NFkappaB translocation in human microvessel endothelial cells using a four-compartment subcellular protein redistribution assay" *J. Biochem. Biophys Meth.* 46, 53–68

[5] Jimi et al. (1998): "Activation of NFkappaB is involved in the survival of osteoclasts promoted by interleukin-1" *J. Biol. Chem* 273, 8799–805

[6] Mejdoubi et al. (1999): "NFkappaB is involved in the induction of the rat hepatic alpha-1 acid glycoprotein gene by phenobarbital" *Biochem Biophys Res. Commun.* 254, 93–9

[7] Butcher et al. (2001): "Toxoplasma gondii tachyzoites inhibit proinflammatory cytokine induction in infected macrophages by preventing nuclear translocation of the transcription factor NFkappaB" *J. Immun.* 167(4), 2193–201

[8] Ott et al. (2001): "Accuracy of two-dimensional electrophoresis for target discovery in human colorectal cancer" The pharmacogenomics Journal-Nature 1(2), 142–51

[9] Lehmann et al. (2001): "Tomato ribonuclease LX with the functional endoplasmic reticulum retention motif HDEF is expressed during programmed cell death processes, including xylem differentiation, germination, and senescence". Plant-Physiol. 127 (2), 436–49

[10] Egesten et al. (1997): "Ribonucleases and host defense: identification, localisation and gene expression in adherent monocytes in vitro". Biochim-Biophys-Acta. 1358 (3), 255–60

[11] Frank et al. (1998): "Cloning, subcellular localisation and functional expression of human RNase HI". Biol-Chem. 379 (12), 1407–12

[12] Dignam et al. (1983):"Accurate transcription initiation by RNA polymerase II in a soluble extract from isolated mammalian nuclei" Nucleic-Acids-Research 11(5), 1475–89

| List of abbreviations | |
|---|---|
| μ | micro |
| 2-DE | two-dimensional gel electrophoresis |
| A431 | epithelial carcinoma cells |
| Bes | N,N-bis(2-hydroxyethyl)-2-aminoethanesulfonic acid |
| CHO | Chinese hamster ovary |
| CMC | critical micelle concentration |
| DAPI | 4',6-diamidino-2-phenylindole |
| DNA | desoxyribonucleic acid |
| DOC | deoxycholate |
| DTT | dithiothreitol |
| EDTA | ethylenediaminetetraacetic acid |
| ELISA | enzyme linked immunosorbent assay |
| EMSA | electrophoretic mobility shift assay |
| F1 | fraction 1, enriched cytosolic proteins |
| F2 | fraction 2, enriched membrane/organelle proteins |
| F3 | fraction 3, enriched nuclear proteins |
| F4 | fraction 4, enriched cytoskeleton proteins |
| H1, H2, . . . , H4 | histone 1, histone 2, . . . , histone 4 |
| HEPES | [4-(2-hydroxyethyl)piperazino]ethanesulfonic acid |
| HLB value | hydrophilic/hydrophobic balance |
| HMG | high motility group |
| HSP70 | heat-shock proteins 70 kDa |
| IEF | isoelectric focusing |
| KDa, kD | kilodaltons |
| L | litres |
| M | molar |
| mA | milliamperes |
| MCF7 | mammacarcinoma cells |
| Mes | 2-morpholinoethanesulfonic acid |
| mg | milligrams |
| $MgCl_2$ | magnesium chloride |
| min | minutes |
| mio | million |
| mmol/l | millimoles per litre |
| MOPS | 3-morpholino-1-propanesulfonic acid |
| MOPSO | 3-(N-morpholino)-2-hydroxypropanesulfonic acid |
| MS | mass spectrometry |
| mV | millivolts |
| MW | molecular weight |
| NaCl | sodium chloride |
| Na-DOC | sodium deoxycholate |
| NP-40 | polyethylene glycol p-isooctyl phenyl ether |
| pI | isoelectric point |
| PIPES | piperazine-1,4-bis(2-ethanesulfonic acid) |
| PVDF | polyvinylidene difluoride |
| RNA | ribonucleic acid |
| RT | room temperature |
| SAOS 2 | osteosarcoma cells |
| SDS | sodium dodecylsulfate |
| SDS-PAGE | sodium dodecylsulfate polyacrylamide gel electrophoresis |
| $T_{25}$ culture bottle | culture bottle with an area of 25 $cm^2$ |
| $T_{75}$ culture bottle | culture bottle with an area of 75 $cm^2$ |
| tris | 2-amino-2-(hydroxymethyl)-1,3-propanediol |
| Triton ® X-100 | octylphenoxypolyethoxyethanol |
| Tween ® 40 | polyoxyethylene sorbitan monopalmitate |
| U | unit |
| ON | overnight |
| V | volts |
| v/v | volume/volume |
| w/v | weight/volume |
| w/w | weight/weight |
| WB | western blotting |

EXAMPLES

Example 1

Investigation of the Protein Pattern by Means of SDS-PAGE of Extracts after Selective Detergent Extraction of Eukaryotic Cells in Accordance with the Prior Art [1, 2, 3].

The starting material for this experiment was mammacarcinoma cells (MCF7) which were confluent to the extent of 80% as adherent cell lawn on a tissue culture dish. The extraction steps were carried out in accordance with the prior art. In this way, protein extracts F1–F4 were obtained. These protein extracts were separated volume-equivalently by means of a 12% polyacrylamide gel in an electric field and visualised using Coomassie Brilliant Blue. An example of this type is shown by FIG. 1.

Figure 1:
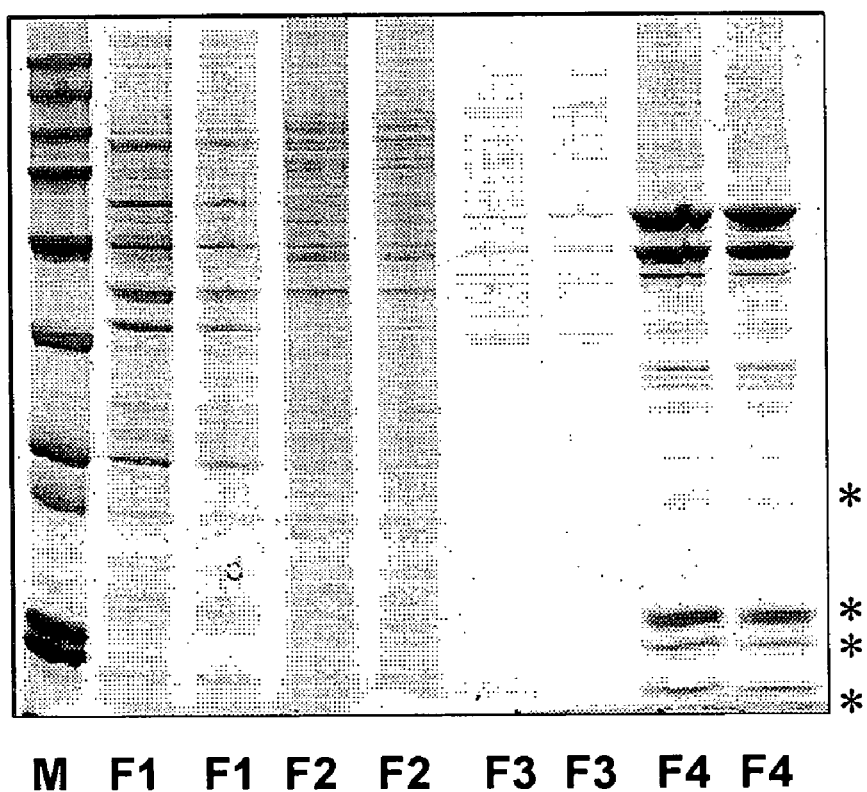
FIGS. 1 and 2 show SDS-PAGE extracts for the prior art

The following terms are used in FIG. 1:

M=marker. F1 denotes fraction 1 containing the cytosolic proteins. F2 stands for fraction 2 and represents the membrane/organelle proteins. F3 demonstrates the fraction 3 referred to in the prior art [1, 2, 3] as 'nuclear' fraction, and F4 signifies fraction 4, which, in accordance with the prior art, is said to contain the proteins of the cytoskeleton and of the nuclear matrix.

A striking feature of the results obtained on reproducing the prior art (see FIG. 1) is the very low protein content of the 'nuclear' fraction 3 compared with fractions 1, 2 and 4. Furthermore, the typical band patterns of the DNA-associated histone proteins (which belong to the group of proteins from the cell nucleus interior) are present in fraction 4, together with the proteins of the cytoskeleton. The typical band patterns of the DNA-associated histone proteins are denoted by an * in FIG. 1.

This result supports the ascertainment of the fact that the method described in the literature [1, 2, 3] for the production of four partial proteomes does not give a partial proteome in which the proteins from the cell nucleus interior are enriched clearly separated from the proteins of the cytoskeleton. The fraction 3 obtainable in accordance with the prior art is not enriched with the proteins from the cell nucleus interior. Rather, the majority of these are located in fraction 4, in which on the one hand the proteins are only obtained in denatured form, and on the other hand the proteins of the cytoskeleton are extracted.

Example 2

Immunoblotting Investigation of the Topological Assignment of Marker Proteins in Extracts after Selective Detergent Extraction of Eukaryotic Cells in Accordance with the Prior Art [1, 2, 3]

The protein extracts obtained in accordance with Example 1 were separated by means of SDS-PAGE and subsequently blotted on a PVDF membrane and investigated using selected marker proteins.

Figure 2:
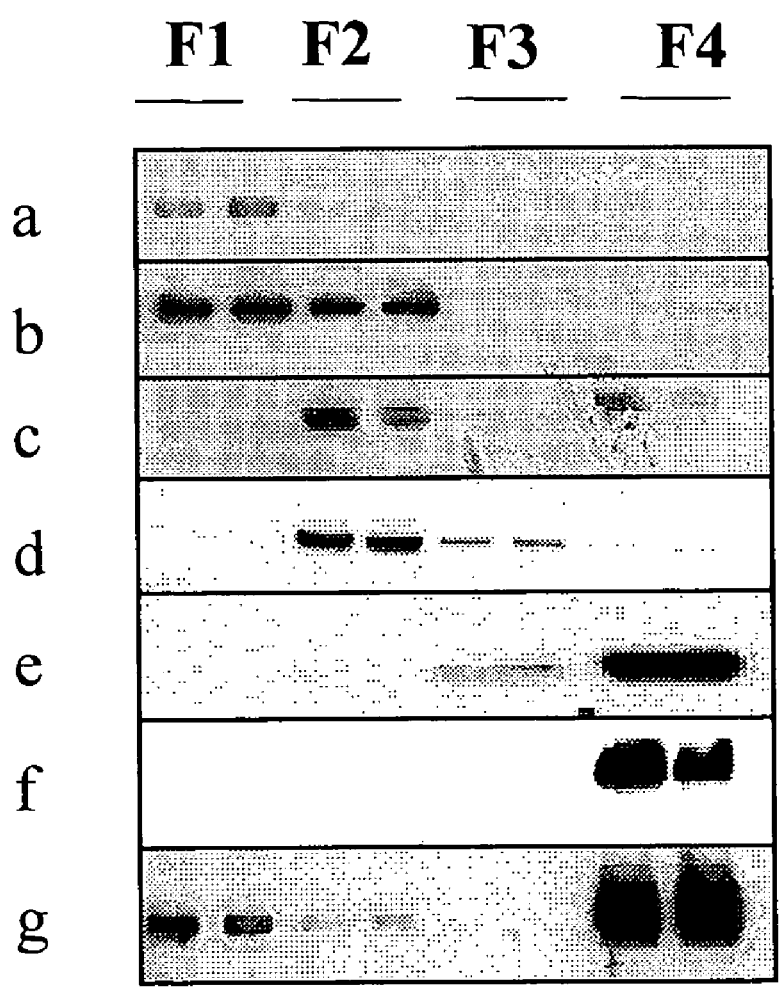

The marker proteins of the cytosol (a–b) and of the membrane/organelles (b–d) are detected in the corresponding fractions (F1 to F4) after extraction of a cell preparation in accordance with the prior art (cf. FIG. 2). However, marker proteins from the cell nucleus interior are not obtained in the corresponding fraction F3, referred to as 'nuclear' fraction, after extraction of a cell preparation in accordance with the prior art. The transcription factor c-jun (e) and the DNA-associated protein histone 1 (f) (both proteins from the cell nucleus interior) are not detected in the 'nuclear' fraction F3, but instead are only liberated in the final fraction (F4) together with the high-abundance cytoskeleton marker cytokeratin (g) under denaturing conditions.

a: calpain; b: HSP 70; c: cadherin; d: cytochrome P 450 reductase; e: c-jun; f: histones; g: cytokeratin The immunoblot analysis of the fractions obtained for representative marker proteins after detergent extraction in accordance with the prior art demonstrates that an independent fraction is not obtained for the soluble and DNA-associated proteins from the cell nucleus interior. Rather, these are solubilised under denaturing conditions together with proteins of the cytoskeleton. Thus, for example, clear analysis of the topological redistribution of the proteins from the cell nucleus interior is not possible using the method in accordance with the prior art.

Example 3

Illustrative Description of Selective Detergent Extraction by the Method According to the Invention The extraction buffers were prepared in accordance with the table under 3a. The extraction is carried out as described in detail under 3b. The results of the method according to the invention are described in greater detail in the following examples.

a. Buffer Composition Used for the Experiment Documented in 3b.

| Buffer | Chemicals | Concentration |
| --- | --- | --- |
| EXTRACTION BUFFER I pH 6.8 | PIPES | 10 mM |
| | Digitonin | 0.02% |
| | Sucrose | 300 mM |
| | Sodium chloride | 15 mM |
| | EDTA | 0.5 mM |
| EXTRACTION BUFFER II pH 7.4 | PIPES | 10 mM |
| | Triton X-100 | 0.50% |
| | Sucrose | 300 mM |
| | Sodium chloride | 15 mM |
| | EDTA | 0.5 mM |
| EXTRACTION BUFFER III pH 7.4 | PIPES | 10 mM |
| | Tween-40 | 1.0% |
| | Deoxycholate | 0.5% |
| | Sodium chloride | 350 mM |
| | Magnesium chloride | 1 mM |
| | Benzonase | 500 U/ml |
| EXTRACTION BUFFER IV pH 7.4 | Sodium dodecylsulfate (SDS) | 5% |
| | Na2HPO4 | 10 mM |
| | NaH2PO4 | 10 mM | b. Illustrative Performance of the Extraction of Adherent Cells

The subcellular fractionation was carried out using tissue culture cells in $T_{25}$ tissue culture dishes. If other culture vessels are used, the amounts of buffer can be scaled up or down correspondingly to the area of the plate used. For the extraction, vital cells in the logarithmic growth phase at about 80% confluence must be employed. In this example, SAOS 2 cells were used.

1. Thaw extraction buffers I, II and III on ice, extraction buffer IV and the protease inhibitor cocktail at RT.
2. Slightly tilt the tissue culture dish so that the medium can be removed from the culture bottle without touching the cell lawn. Carefully remove media residues.
3. Slightly tilt the tissue culture dish. Carefully pipette in 2 ml of ice-cold washing buffer from the edge, covering the cell lawn. Incubate the culture dish at 4° C. for 5 min while shaking gently.
4. Slightly tilt the tissue culture dish and carefully remove the washing buffer without touching the cell lawn.
5. Repeat steps 3 and 4 in order completely to remove medium constituents, such as, for example, BSA, amino acids and indicator dyes.
6. Mix 1 ml of ice-cold extraction buffer I and 5 μl of protease inhibitor cocktail with one another. Carefully pipette onto the washed tissue culture dish from the edge without touching the cell lawn. Carefully cover the cells with the buffer. Incubate at +4° C. for 10 min while shaking gently.
7. Carefully tilt the tissue culture dish. Carefully remove the cytosolic protein extracts (fraction 1) from the culture bottle without touching the cell lawn and store on ice until used on the same day. For long-term storage, aliquot in suitable amounts (for example 100 µl) and store at −80° C.
8. Mix 1 ml of ice-cold extraction buffer II and 5 µl of protease inhibitor cocktail with one another. Carefully pipette into the tissue culture dish from the edge without touching the cell lawn. Carefully cover the cells with the buffer, then incubate at +4° C. for 30 min while shaking gently.
9. Carefully tilt the tissue culture dish. Carefully remove the extract containing the membrane/organelle proteins (fraction 2) from the culture bottle without touching the cell lawn and incubate on ice until used on the same day. For longer-term storage, aliquot in suitable amounts and store at −80° C.
10. Mix 500 µl of ice-cold extraction buffer III, 5 µl of protease inhibitor cocktail and 10 µl (250 U) of Benzonase® with one another and carefully pipette onto the remaining cell constituents. Incubate at 4° C. for 10 min while shaking gently.
11. Carefully tilt the tissue culture bottle. Carefully remove the protein extract containing the nuclear proteins (fraction 3) from the culture bottle without touching the cell lawn and store on ice until used on the same day. For long-term storage, aliquot in suitable amounts and store at −80° C.
12. Mix 500 µl of extraction buffer IV adjusted to room temperature and 5 µl of protease inhibitor cocktail with one another and add to the remaining cell lawn. The cell layer detaches from the plate on addition of this buffer.
13. Suspend by pipetting up and down using a 1 ml pipette tip (for example Eppendorf). After complete dissolution of the remaining cell constituents, transfer into a microcentrifuge tube and store on ice until used on the same day. Fraction 4 contains cytoskeleton proteins. For long-term storage, aliquot in suitable amounts and store at −80° C.

Example 4

Morphological Portrayal of the Cells When Carrying Out the Selective Detergent Extraction in Accordance with the Invention The protein extraction was carried out analogously to Example 3 from a cell culture in a $T_{75}$ culture bottle (grown 80% confluently with SAOS 2 cells). These were investigated microscopically for morphological changes as a consequence of the method before the extraction, i.e. in untreated form (picture i), and stepwise after the respective selective detergent extraction (pictures ii–iv).

Figure 3:
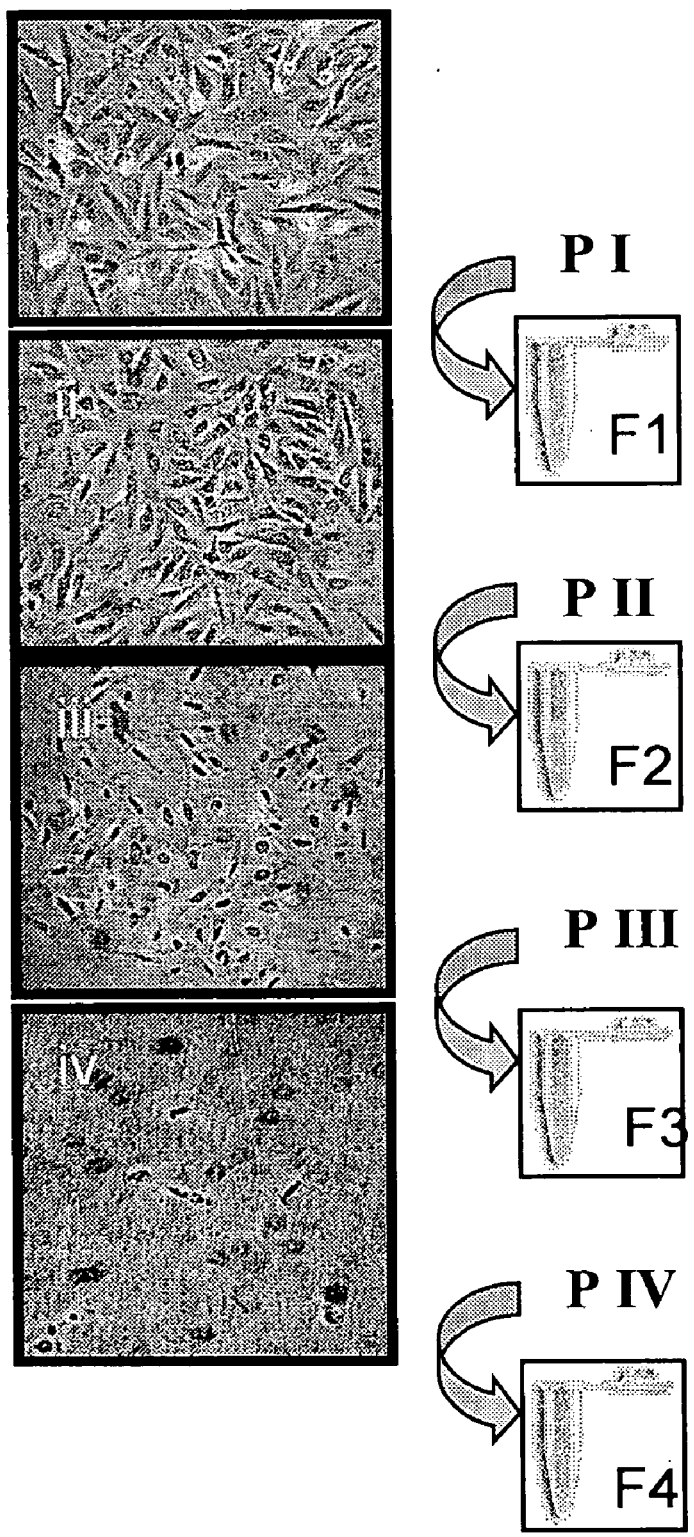
FIG. 3 portrays the morphology of cells during the extractions of the invention

FIG. 3 shows an example of this type. After treatment of the cells with extraction buffer I (picture ii), the cytosolic contents of the cells escape, whereupon the cells shrink. The integrity of the cell nuclei and plasma membrane is substantially retained. After incubation of the cells with extraction buffer II (picture iii), the membrane/organelle proteins are extracted without impairing the integrity of the cell nuclei. After incubation of the remaining cell material with extraction buffer III (method step c) according to the invention) (picture iv), the fraction of the proteins from the cell nucleus interior is extracted. The remaining cell material is taken up in extraction buffer IV, giving a fraction containing the cytoskeleton constituents.
P I: extraction buffer I
P II: extraction buffer II
P III: extraction buffer III
P IV: extraction buffer IV
i: SAOS 2 cells, untreated
ii: SAOS 2 cells treated with extraction buffer I, incubation gives fraction 1 (F1)
iii: SAOS 2 cells treated with extraction buffer II, incubation gives fraction 2 (F2)
iv: SAOS 2 cells treated with extraction buffer III, incubation gives fraction 3 (F3)

Example 5

Protein Distribution in Extracts after Selective Detergent Extraction of Eukaryotic Cells in Accordance with the Prior Art [1, 2, 3] Compared with the Method According to the Invention In the method according to the invention, the concentration of an alkali metal salt in extraction buffer III was increased in this example compared with the prior art [1, 2, 3], and in addition a nuclease was employed. In order to document the improvement achieved, extraction buffer III was prepared with varying salt concentrations (prior art, 15 mM NaCl+Benzonase®, 150 mM NaCl+Benzonase® and 350 mM NaCl+Benzonase®). The Benzonase® (nonspecific endonuclease) was employed in the same concentration in all experiments. All other parameters correspond to those indicated in the prior art. The biological material employed was 4 times about 80% confluent SAOS 2 cells. The protein extracts obtained were analysed and evaluated by means of a protein determination method based on the Lowry assay.

The method according to the invention indicates more efficient extraction of the cell nucleus. This is clearly evident from a significant increase in the protein content of the nuclear fraction (F3) and a decrease in the amount of protein in the cytoskeleton fraction (F4).

Figure 4:
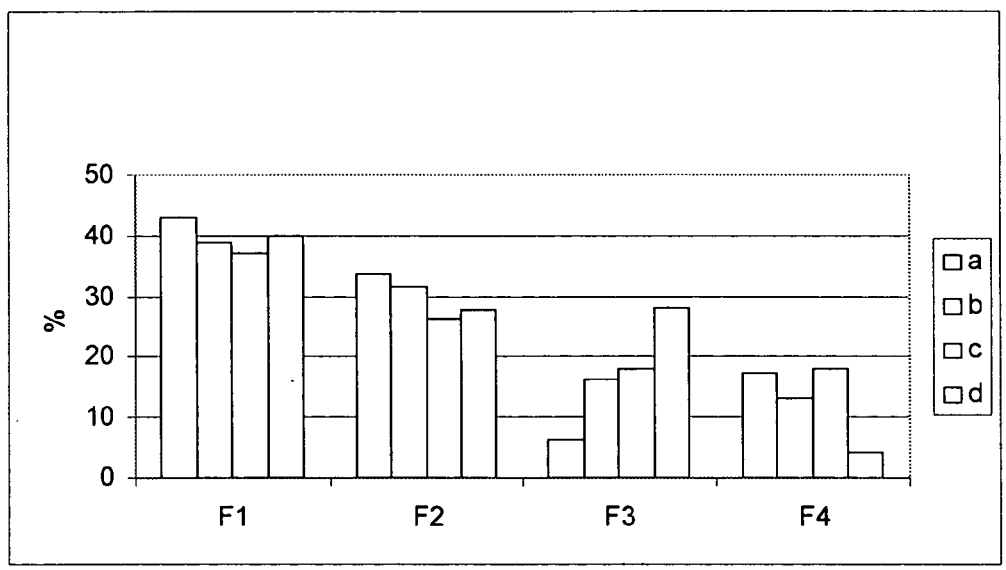
FIG. 4 shows results of protein determination and distribution over four fractions

FIG. 4 shows the results of the protein determination and the distribution thereof over the four fractions.

The increase in the salt concentration in buffer III enables a redistribution of proteins from fraction 4 (F4) into fraction 3 (F3) to be achieved in connection with the action of Benzonase®. As expected, no significant change in fractions F1 and F2 is observed.
a) Prior art
b) 15 mM NaCl in buffer III+Benzonase (prior art+Benzonase)
c) 150 mM NaCl in buffer III+Benzonase
d) 350 mM NaCl in buffer III+Benzonase Example 6

Investigations of the Action of the Extraction Buffer According to the Invention (Buffer III) with and without Addition of a Nuclease The distribution of marker proteins for the corresponding fractions was likewise investigated in the protein extracts from Example 5 by means of immunological methods after separation by SDS-PAGE and blotting on a PVDF membrane.

Figure 5:
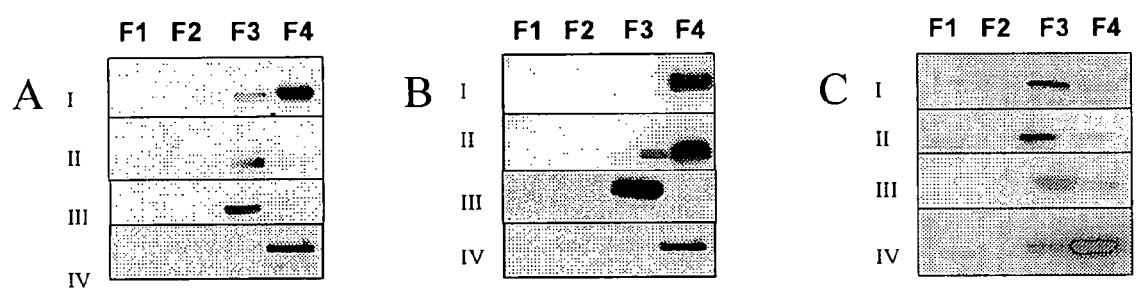
FIGS. 5A–C show distribution of transcription factors and proteins

The analysis shown in FIG. 5 demonstrates the distribution of transcription factors (through the example of c-jun FIG. 5A) and DNA-associated proteins (through the example of histone 1 FIG. 5B) in fractions after selective detergent extraction depending on the NaCl concentration and the action of a nuclease. The integrity of the cytoskeleton is not significantly impaired.

In order to test the action of the Benzonase®, the behaviour of the transcription factors and histone proteins was investigated in the presence of 350 mM NaCl in extraction buffer III, with and without the action of nuclease in fraction 3 (FIG. 5C). The use of nuclease with constant NaCl concentration facilitates a clearly increased recovery rate of the DNA-associated histone proteins in fraction 3, whereas the transcription factors can be extracted in the presence of 350 mM NaCl without the action of nuclease.

Detailed Description of FIG. 5:

5A) The recovery rate of the transcription factor c-jun in fraction 3 is dependent on the NaCl concentration in buffer III. From a concentration of 150 mM NaCl in buffer III, c-jun can be detected in fraction 3 (I: c-jun/15 mM NaCl; II: c-jun/150 mM NaCl; III c-jun/350 mM NaCl). None of these conditions impairs the integrity of the cytoskeleton, which is documented by the exclusive detection of cytokeratin in fraction 4 (IV: cytokeratin/350 mM NaCl). In all experiments, Benzonase® was employed. On extraction in accordance with the prior-art protocol [1, 2, 3], c-jun is detected in the fourth fraction (I).

5B) The behaviour of histone 1 at different salt concentrations in buffer III. The DNA-associated protein histone 1 was only detected at 350 mM NaCl in buffer 3 and simultaneous nuclease action in fraction 3 (I: histone 1/15 mM NaCl; II: histone 1/150 mM NaCl; III: histone 1/350 mM NaCl). On extraction in accordance with the prior-art protocol [1, 2, 3], histone 1 is found in the fourth fraction (I).

5C) c-jun is detected in the presence of 350 mM NaCl in extraction buffer Ill, independently of the nuclease action in fraction 3 (I: c-jun/buffer III with Benzonase; II: c-jun/buffer III without Benzonase). Histone 1, by contrast, required the simultaneous action of nuclease in order to be detected together with c-jun in fraction 3 (III: histone/buffer III with Benzonase; IV: histone/buffer III without Benzonase). The use of the nuclease at a constant NaCl concentration facilitates a clearly increased recovery rate of DNA-associated proteins in fraction 3.

Example 7

Morphological Portrayal of Cell Compartment/Organelles on Performance of the Selective Detergent Extraction in Accordance with the Invention The selectivity of the extraction method according to the invention for the corresponding subcellular partial proteomes was documented by fluorescence microscopy. The protein extraction according to the invention was carried out with a cell preparation of transfected COS-1 cells, otherwise analogously to Example 3. The cells were investigated for morphological changes as a consequence of the method by fluorescence microscopy before the extraction, i.e. after washing (picture I), and stepwise after the respective extraction step (pictures II–V).

Figure 6:
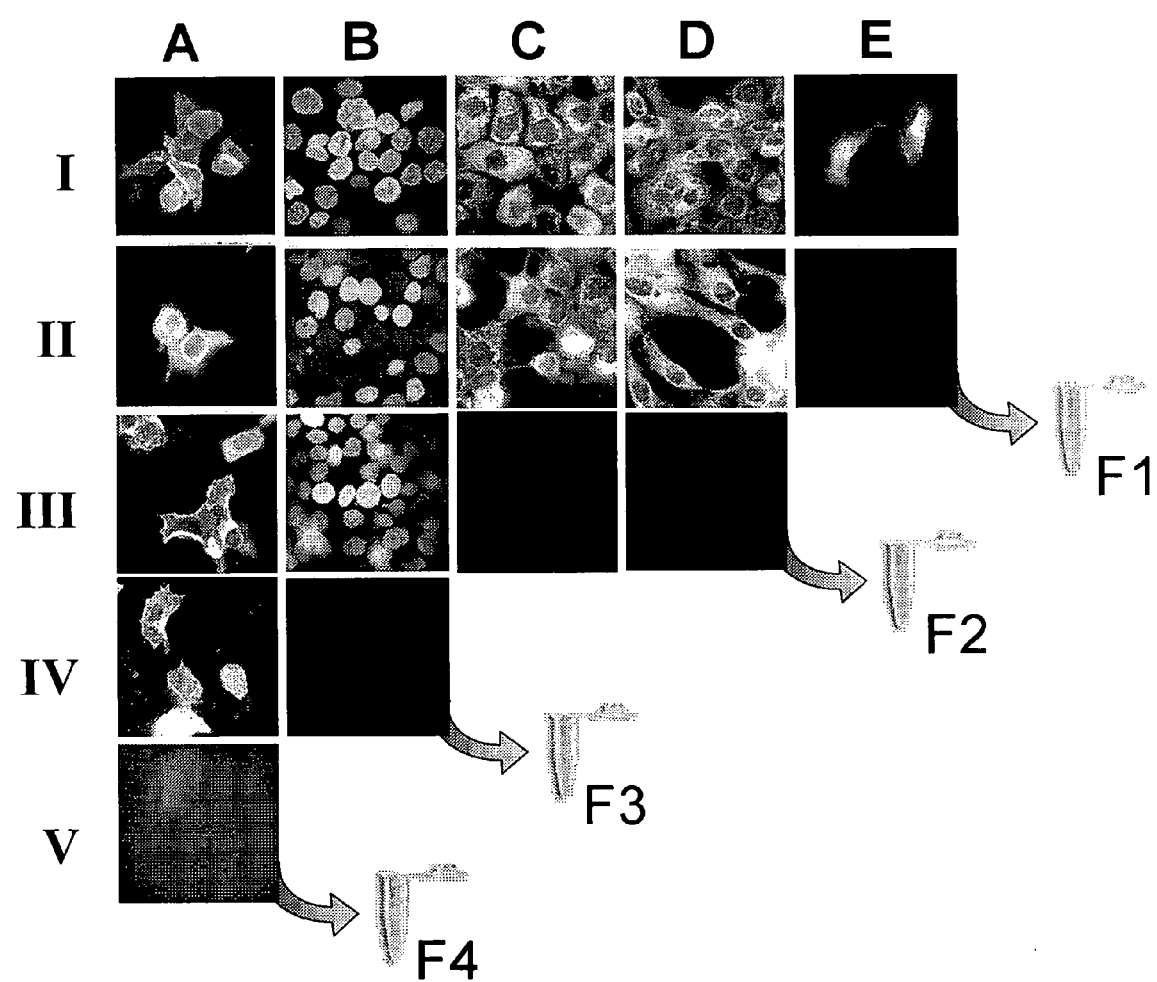
FIG. 6 shows subcellular compartments during extraction

FIG. 6 shows the subcellular compartments or organelles during the extraction according to the invention through the example of COS-1 cells. Washing of the cells for the removal of medium constituents which would otherwise interfere does not impair the morphology of the cells (picture I). After treatment of the cells with extraction buffer I (picture II), the cytosolic contents of the cells escape, with the integrity of the cell organelles, of the cell nuclei and of the cytoskeleton being very substantially retained. After incubation of the cells with extraction buffer II (picture III), the membrane/organelle proteins are extracted, with the integrity of the cell nuclei and of the cytoskeleton still being retained. After incubation of the remaining cell material with extraction buffer III (method step c) according to the invention) (picture IV), the fraction of the proteins from the cell nucleus interior is extracted, with the integrity of the cytoskeleton being very substantially retained. The remaining cell material is taken up in extraction buffer IV, giving a fraction containing the cytoskeleton constituents.

F 1: fraction 1
F 2: fraction 2
F 3: fraction 3
F 4: fraction 4

FIG. 6 demonstrates the selectivity of the method according to the invention with reference to the visualisation of subcellular compartments or organelles of transfected COS-1 cells by means of commercially available fluorescent dyes: phallicidin for staining the filamentary actin cytoskeleton, DAPI for visualisation of the cell nuclei, ER-Tracker™ for visualisation of the endoplasmatic reticulum, MitoTracker for visualisation of the mitochondria (as membrane/organelle marker) and soluble, green-fluorescent protein (GFP), which is expressed by the transfected COS-1 cells, and is used as marker protein for the cytoplasm.

Description of FIG. 6:

A: phallicidin, B: DAPI staining, C: MitoTracker, D: ER-Tracker™, E: GFP

I: transfected COS-1 cells, untreated
II: transfected COS-1 cells treated with extraction buffer I, incubation gives fraction 1 (F1)
III: transfected COS-1 cells, after treatment with extraction buffer I additionally treated with extraction buffer II, incubation gives fraction 2 (F2)
IV: transfected COS-1 cells, after treatment with extraction buffers I and II additionally treated with extraction buffer III, incubation gives fraction 3 (F3)
V: transfected COS-1 cells, after treatment with extraction buffers I to III additionally treated with extraction buffer IV, incubation gives fraction 4 (F4)

Example 8

Protein Patterns of Extracts and Topological Assignment of Subcellular Marker Proteins after Selective Detergent Extraction of Eukaryotic Cells by Extraction Methods According to the Invention The protein extracts obtained by extraction in accordance with the invention of SAOS 2 cells as described in Examples 3a and 3b were separated by means of SDS-PAGE (10% tricine-PAA gel). The proteins were subsequently detected using Coomassie Brilliant Blue. A result of this type is shown in FIG. 7A.

In addition, the protein extracts were blotted on PVDF membranes after separation by SDS-PAGE and investigated by immunoblot analysis against selected marker proteins. The results are shown in FIG. 7B.

In agreement with the protein amount determination in Example 4 and the morphological findings in Example 6, it can be demonstrated here (7A and 7B) that efficient liberation of DNA-associated proteins from the cell nucleus interior is facilitated without impairing the integrity of the cytoskeleton in the process. After extraction in accordance with the invention of a cell preparation as described in Example 3, an independent fraction of the proteins from the cell nucleus interior is thus obtained, which thus allows for the first time the separate consideration of functional proteins from the cell nucleus and cytoskeleton without the loss of other partial proteomes.

Figure 7:
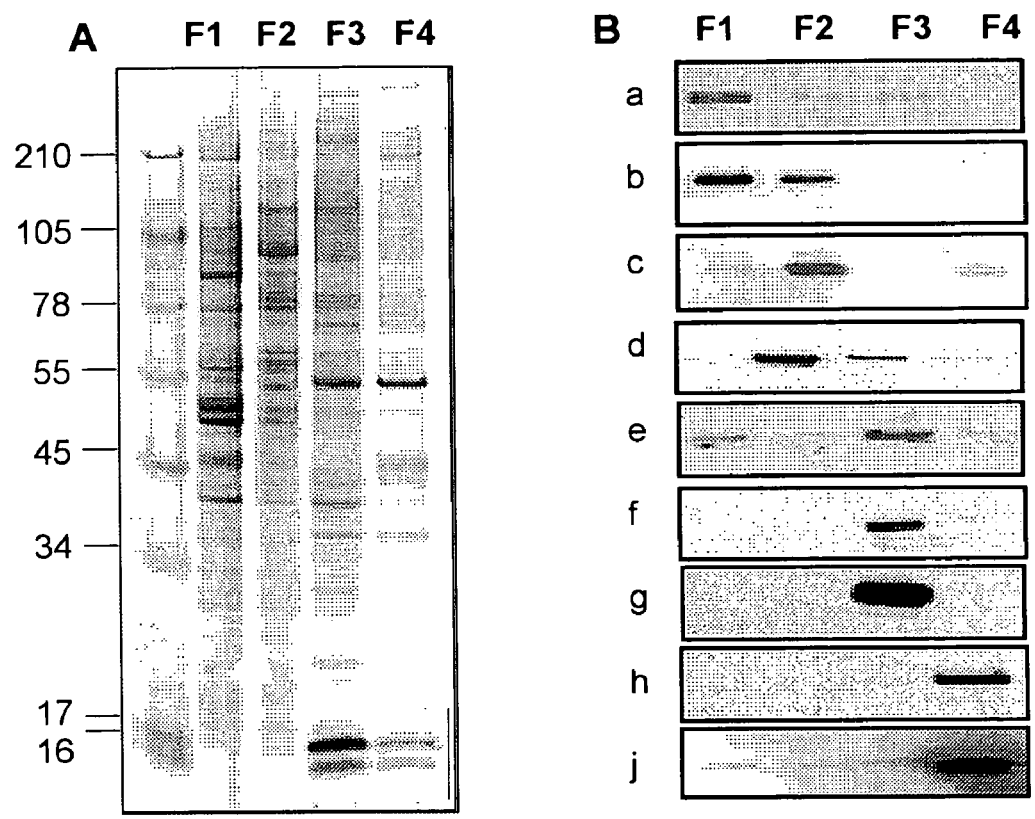
FIGS. 7A–B show SDS-PAGE separations for the invention

Detailed Description of FIG. 7:

7A) After selective detergent extraction of eukaryotic cells by the method according to the invention, different protein patterns of the independent subcellular fractions can clearly be observed. F1 here denotes fraction 1 containing the cytosolic proteins. F2 stands for fraction 2 and represents the membrane/organelle proteins. F3 (fraction 3) corresponds to the proteins from the cell nucleus interior. F4 (fraction 4) finally represents the proteins of the cytoskeleton and of the nuclear matrix. Compared with extraction in accordance with the prior art [1, 2, 3] (FIG. 2), significantly more proteins are detected in fraction 3.

7B) Distribution of Marker Proteins Over Subcellular Fractions after Selective Detergent Extraction After selective detergent extraction of eukaryotic cells by the method according to the invention, a clear topological assignment of nuclear marker proteins is possible, in contrast to the prior art (FIG. 3). Marker proteins of the cytosol and of the membrane/organelles are detected in the corresponding fractions (a–d). Soluble transcription factors (e and f) and the DNA-associated protein histone 1 (g) are clearly enriched in a fraction of the proteins from the cell nucleus interior. Only in the final step is the high-abundance cytoskeleton marker cytokeratin (h and j) extracted separately therefrom.

a: calpain; b: heat-shock protein 70 (HSP 70); c: cadherin; d: cytochrome P 450 reductase; e: c-fos; f: c-jun; g: histones; h: cytokeratin; j: vimentin Example 9

Protein Patterns of Extracts and Topological Assignment of Subcellular Marker Proteins after Selective Detergent Extraction of Intestinal Cancer Tissue by Extraction Methods According to the Invention Starting from intestinal cancer tissue, cell clusters were produced by standard methods [8] and treated by the extraction method according to the invention. Extracts resulting therefrom were separated by means of SDS-PAGE, transferred to PVDF membranes and investigated by immunoblot analysis against selected marker proteins. The selected marker proteins are as follows:

I=calpain, II=cytochrome p 450 reductase, III=c-jun.

Figure 8:
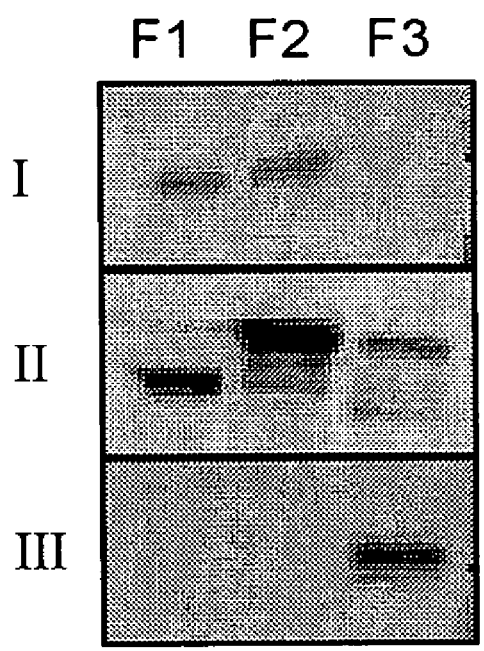
FIG. 8 shows protein patterns of extracts

In this FIG. 8, F1 denotes fraction 1 containing the cytosolic proteins. F2 stands for fraction 2 and represents the membrane/organelle proteins. F3 (fraction 3) corresponds to the proteins from the cell nucleus interior. The remaining cell material, which can be taken up in extraction buffer IV, was not investigated in this example. The immunoblot analysis with selected marker proteins confirms the suitability of selective detergent extraction by extraction methods according to the invention for use with cell preparations from tissue prepared by standard methods [8].

Example 10

Figure 9:
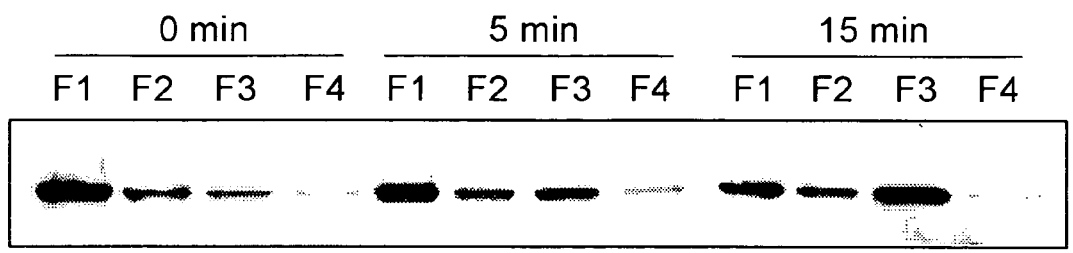
Figure 9:
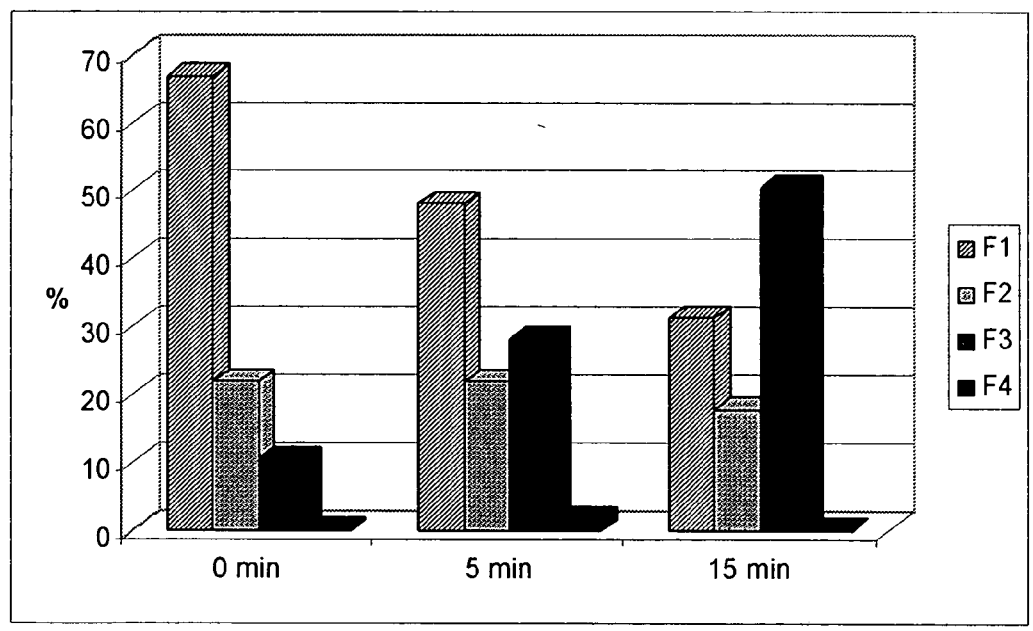

Investigation of the Dynamic Subcellular Redistribution of NFkappaB which is Involved in Signal Transduction and, after Cellular Stimulation with TNFalpha from the Cytosol, is Translocated into the Cell Nucleus A431 cells were stimulated with TNFα for various times (0, 5 and 15 minutes) and extracted in accordance with the method according to the invention (see Example 3). The cytosolic fraction (F1), the membrane/organelle fraction (F2), the nuclear fraction (fraction of the proteins from the cell nucleus interior) (F3) and the cytoskeleton fraction (F4) were separated by means of SDS-PAGE for the respective stimulation time. An immunoblot was subsequently carried out with a specific antibody against NFkappaB. The time analysis clearly demonstrates a redistribution of NFkappaB from the cytosol into the cell nucleus. FIG. 9a shows the results of the immunoblot analysis. The intensity of the protein bands was determined by densitometry. The data measured were shown graphically in relation to one another (see FIG. 9b).

The method according to the invention is suitable for analysing the dynamic subcellular redistribution of NFkappaB, which is involved in signal transduction and is translocated from the cytosol into the cell nucleus after cellular stimulation with TNFalpha, simply and directly by means of immunoblot.

Example 11

The Detection of Endogenous Enzyme Activities after Selective Detergent Extraction of Eukaryotic Cells using the Extraction Method According to the Invention Demonstrates Both Selectivity and Functionality of Representative Enzymes in Extracts I, II and III After selective detergent extraction of eukaryotic cells by means of the method according to the invention, enzyme activities of representative marker enzymes were investigated. The activities for calpain (a), as marker enzyme for the cytoplasm, for alkaline phosphatase (b), as marker enzyme for membrane/organelles, and for endogenous cellular RNases (c) were determined here. RNases are enzymes which can occur in a plurality of forms within the cell and may be associated with different subcellular compartments depending on the cell type and specific factors. For protection of cellular RNA, RNase is usually in compartmentalised form. Thus, for example, on the one hand RNase LX [9] and also a number of RNase A subtypes were previously found associated with membrane/organelles [10], on the other hand RNase HII is localised in the cell nucleus [11].

For the determination of the enzyme activity, cell extracts were employed which had been prepared in accordance with the invention in accordance with the procedure in Example 3. In the case of the determination of the calpain activity as marker enzyme for the cytoplasm, cell preparations of human skin cancer cells (A 431) were employed for this purpose, for the determination of the activity of alkaline phosphatase as marker enzyme for membrane/organelles (b), cell extracts from SAOS 2 cells were employed. In order to document that the fraction of the cell nuclear proteins is also obtained in the native state after extraction in accordance with the invention of cell preparations, the endogenous activity of the cellular RNases, which also occur in the cell nucleus (see above), was determined. In order to enable determination of the activity of these endogenous RNases, additional cell extracts from SAOS 2 cells were prepared, with no nuclease being added to extraction buffer III for this purpose.

Figure 10:
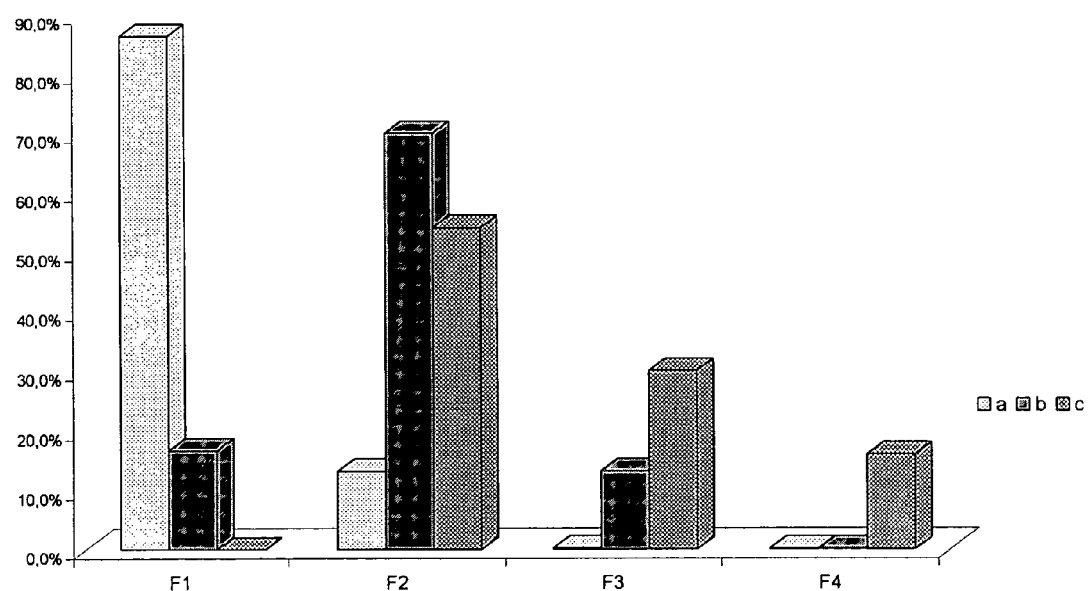

The results are shown graphically in FIG. 10, and demonstrate the selectivity of the method according to the invention for cell fractionation in agreement with the morphological findings (FIG. 6) and the results from the immunoblot analysis (FIG. 7). About 90% of the calpain activity determined can be detected in the fraction assigned to the cytoplasm. The activity of the alkaline phosphatase employed as membrane marker is detected to the extent of more than 70% in the membrane/organelle fraction. The activity of cellular RNases after extraction in accordance with the invention without the addition of nuclease is distributed as follows: 54% in the membrane/organelle fraction, 30% in the fraction of the cell nuclear proteins and 16% in the fraction of the cytoskeleton proteins. No RNase activity was found in the cytoplasm fraction. The extraction buffers employed in accordance with the invention, particularly those for the production of the partial proteome of the proteins from the cell nucleus interior, yield active, non-denatured proteins. The method according to the invention is thus suitable for the analysis of the subcellular distribution of enzyme activities.

F1–F4 denote fractions 1–4. The relative enzyme activities for calpain (a), alkaline phosphatase (b) and RNase (c) are shown graphically in this figure.

Example 12

The Fraction of the Proteins from the Cell Nucleus Interior Contains Functional Transcription Factors which are Active with Respect to DNA Binding CHO-K1 cells were extracted by the extraction method according to the invention (as described in Example 3), but without the addition of Benzonase® to extraction buffer III (FIG. 11A). A fraction of the proteins from the cell nucleus interior containing active transcription factors, which was obtained by a standard method for the specific preparation of nuclear extracts [12], was likewise employed as positive control (FIG. 11B).

Samples of the nuclear fractions obtained were subsequently analysed by EMSA in order to determine the binding activity present of transcription factors to an Oct1 oligonucleotide. The analysis clearly demonstrates that the nuclear fraction contains functional transcription factors which are active with respect to DNA binding after the method according to the invention. This is an illustrative demonstration of the broad applicability of the method according to the invention.

Figure 11:
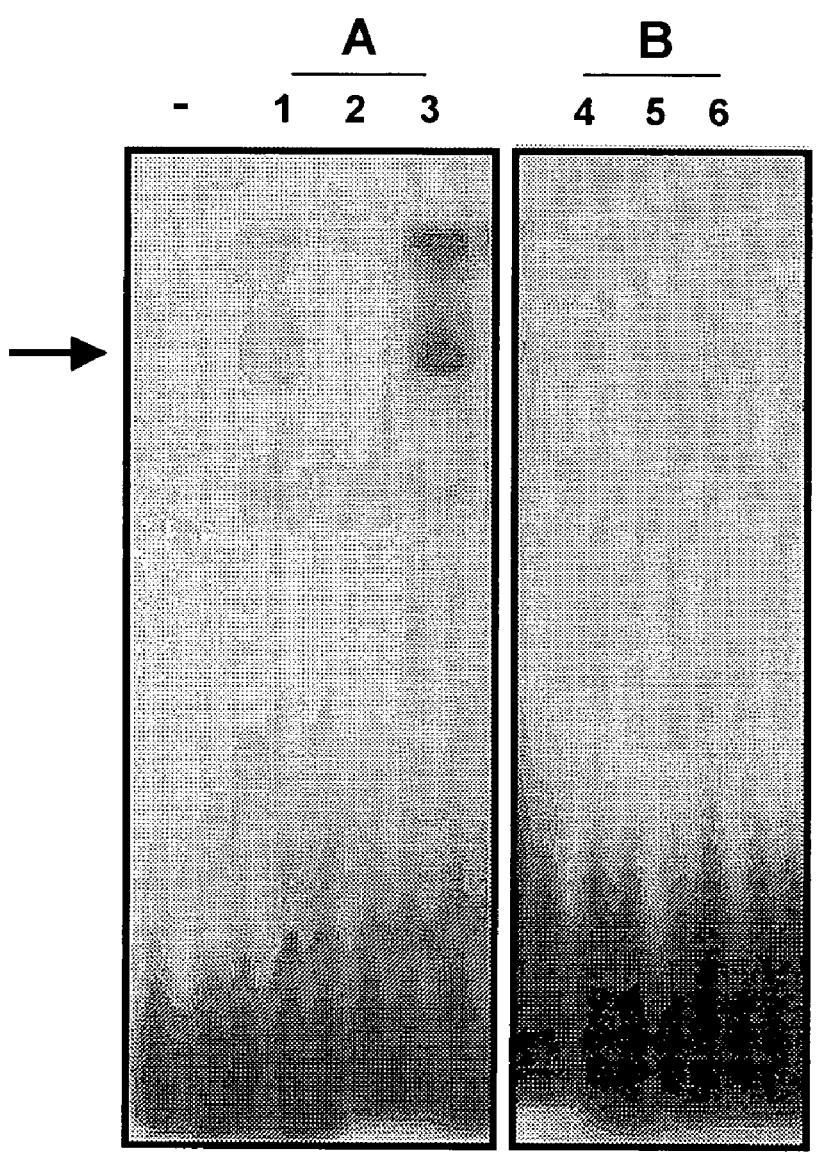

Description of FIG. 11:
1. Fraction of the proteins from the cell nucleus interior obtained in accordance with the invention
2. Fraction of the proteins from the cell nucleus interior obtained in accordance with the invention+100× non-radioactively labelled Oct1 sample
3. Fraction of the proteins from the cell nucleus interior obtained in accordance with the invention+100× non-radioactively labelled SP1 sample
4. Fraction of the proteins from the cell nucleus interior obtained by standard methods
5. Fraction of the proteins from the cell nucleus interior obtained by standard methods+100× non-radioactively labelled Oct1 sample
6. Fraction of the proteins from the cell nucleus interior obtained by standard methods+100× non-radioactively labelled SP1 sample

The invention claimed is:

1. A method for the sequential production of partial proteomes from a complete proteome of a cell preparation comprising:
   a) providing a sample containing a cell preparation
   b) extracting the cytosolic proteins and the membrane/organelle proteins from the sample provided in step a), leaving a cell nucleus preparation, and
   c) extracting the proteins from the cell nucleus interior from the preparation obtained in step b) by treating with an extraction buffer having a pH of between 6.5 and 8 which comprises:
      in total from 0.1 to 7 percent by weight of one or more nonionic detergents
      in total from 0.05 to 3 percent by weight of one or more cholic acid derivatives, and
      one or more salts of alkali metal and/or ammonium in a total concentration of between 75 and 500 mmol/l,
      wherein detergent-resistant proteins of the cytoskeleton and of the nuclear matrix are not extracted to a significant extent together with the proteins from the cell nucleus interior, but instead remain in the extraction residue.

2. A method for the sequential production of partial proteomes from a complete proteome of a cell preparation comprising:
   a) providing a sample containing a cell preparation,
   b) extracting the cytosolic proteins and the membrane/organelle proteins from the sample provided in step a), leaving a cell nucleus preparation, and
   c) extracting the proteins from the cell nucleus interior from the preparation obtained in step b) by treating with an extraction buffer having a pH of between 6.5 and 8 which comprises:
      in total from 0.1 to 7 percent by weight of one or more nonionic detergents,
      in total from 0.05 to 3 percent by weight of one or more cholic acid derivatives, and
      one or more salts of alkali metal and/or ammonium in a total concentration of between 75 and 500 mmol/l,
      wherein the extract obtained in step c) is a partial proteome enriched with proteins from the cell nuceleus interior.

3. A method of claim 2 wherein the partial proteome comprises histone and/or non-histone proteins.

4. A method of claim 3 wherein the partial proteome comprises HMG proteins, transcription factors, RNA binding proteins, and/or skeleton proteins of the cell interior.

5. A method according to claim 2, wherein the extraction buffer employed in step c) additionally comprises a nuclease.

6. A method of claim 5, wherein said nuclease is an endonuclease from *Serratia marcescens*.

7. A method according to claim 2, wherein the extraction buffer employed in step c) comprises polyoxyethylene sorbitan monopalmitate as nonionic detergent, deoxycholate as cholic acid derivative and NaCl as alkali metal salt.

8. A method according to claim 2, wherein step b) comprises:
   b i) extracting the cytosolic proteins from the sample provided in step a) by selective permeabilization of the plasma membrane without significantly impairing the integrity of the subcellular membrane/organelle structures, the cell nucleus and the cytoskeleton
   b ii) extracting the membrane/organelle proteins from the part of the sample remaining after the extraction in step b i) with retention of the structural integrity of cell nucleus and cytoskeleton.

9. A method according to claim 2, wherein the proteins of the detergent-resistant cytoskeleton and of the nuclear matrix are, in an additional method step d), extracted as a further partial proteome from the extraction residue remaining in step c).

10. A method of claim 2 wherein step b) comprises treatment of with a non-ionic detergent or a zwitterionic detergent under mild conditions.

11. A method of claim 10, wherein said detergent comprises octylphenoxypolyethoxyethanol or polyethylene glycol p-isooctyl phenyl ether.

12. A method of claim 2, wherein said extraction buffer has a pH of between 6.9 and pH 7.8.

13. A method of claim 2, wherein said extraction buffer comprises MOPSO, BES, MOPS, phosphate or PIPES at a concentration from between 2 and 100 mM.

14. A method of claim 2, wherein said non-ionic detergent comprises 0.2 and 5% by weight of polyoxyethylene sorbitan monopalmitate and said cholic acid derivative comprises 0.1 to 2.5% by weight of Na deoxycholate.

15. A method of claim 2, wherein said extraction buffer comprises 10 mM PIPES, 1% by weight of polyoxyethylene sorbitan monopalmitate, 0.5% by weight of Na deoxycholate and 350 mM NaCl.

16. A protein extraction kit at least containing an extraction buffer having a pH of between 6.5 and 8 which further comprises:
   in total from 0.1 to 7 percent by weight of one or more nonionic detergents
   in total from 0.05 to 3 percent by weight of one or more cholic acid derivatives
   one or more salts from the group consisting of the ammonium and/or alkali metal salts in a total concentration of between 75 and 500 mmol/l.

17. A kit according to claim 16, additionally containing a nuclease.

18. A kit of claim 17, wherein said nuclease is an endonuclease from *Serratia marcescens*.

19. A kit according to claim 16, additionally containing a buffer for extraction of the cytosolic proteins and/or the membrane/organelle proteins from cell preparations and a buffer for extraction of the proteins of the detergent-resistant cytoskeleton and of the nuclear matrix.

20. A kit of claim 16, wherein said extraction buffer has a pH of between 6.9 and pH 7.8.

21. A kit of claim 16, wherein said extraction buffer comprises MOPSO, BES, MOPS, phosphate or PIPES at a concetration from between 2 and 100 mM.

22. A kit of claim 16, wherein said non-ionic detergent comprises 0.2 and 5% by weight of polyoxyethylene sorbitan monopalmitate and said cholic acid derivative comprises 0.1 to 2.5% by weight of Na deoxycholate.

23. A kit of claim 16, wherein said extraction buffer comprises 10 mM PIPES, 1% by weight of polyoxyethylene sorbitan monopalmitate, 0.5% by weight of Na deoxycholate and 350 mM NaCl.

* * * * *

UNITED STATES PATENT AND TRADEMARK OFFICE
CERTIFICATE OF CORRECTION

PATENT NO. : 7,262,283 B2  Page 1 of 1
APPLICATION NO. : 10/525991
DATED : August 28, 2007
INVENTOR(S) : Robertus Hendriks et al.

It is certified that error appears in the above-identified patent and that said Letters Patent is hereby corrected as shown below:

On the title page item [75] Inventors: Add third inventor -- Jonas Anders, Darmstadt (DE) --
Column 22, line 2, reads "detergents" should read -- detergents, --
Column 22, line 63, reads "treatment of with" should read -- treatment with --
Column 23, line 2, reads "pH 7.8." should read -- 7.8. --
Column 23, line 5, reads "concentration from between" should read -- concentration of between --
Column 23, line 7, reads "comprises 0.2 and 5%" should read -- comprises 0.2 to 5% --
Column 24, line 10, reads "pH 7.8." should read -- 7.8. --
Column 24, line 14, reads "concetration from between" should read -- concentration of between --
Column 24, line 16, reads "comprises 0.2 and 5%" should read -- comprises 0.2 to 5% --

Signed and Sealed this

Second Day of March, 2010

David J. Kappos
*Director of the United States Patent and Trademark Office*